US012594110B2

(12) United States Patent
Brojek

(10) Patent No.: US 12,594,110 B2
(45) Date of Patent: Apr. 7, 2026

(54) CRYOSURGICAL PROBE AND METHOD OF MANUFACTURING THEREOF

(71) Applicant: Metrum Cryoflex S.A., Stare Babice (PL)

(72) Inventor: Wieslaw Brojek, Janow (PL)

(73) Assignee: Metrum Cryoflex S.A., Stare Babice (PL)

( * ) Notice: Subject to any disclaimer, the term of this patent is extended or adjusted under 35 U.S.C. 154(b) by 1001 days.

(21) Appl. No.: 17/644,468

(22) Filed: Dec. 15, 2021

(65) Prior Publication Data

US 2023/0181230 A1      Jun. 15, 2023

(51) Int. Cl.
*A61B 18/02* (2006.01)
*F25B 9/02* (2006.01)
*A61B 18/00* (2006.01)

(52) U.S. Cl.
CPC .............. *A61B 18/02* (2013.01); *F25B 9/02* (2013.01); *A61B 2018/00101* (2013.01); *A61B 2018/00148* (2013.01); *A61B 2018/0212* (2013.01); *A61B 2018/0237* (2013.01); *F25B 2309/003* (2013.01); *F25B 2309/021* (2013.01)

(58) Field of Classification Search
CPC .......... A61B 18/02; A61B 2018/00101; A61B 2018/00148; A61B 2018/0212; A61B 2018/0237; F25B 9/02; F25B 2309/003; F25B 2309/021
See application file for complete search history.

(56) References Cited

U.S. PATENT DOCUMENTS 5,254,116 A * 10/1993 Baust ..................... A61B 18/02
607/105
5,423,807 A    6/1995 Milder
(Continued)

FOREIGN PATENT DOCUMENTS

CN        1212103 C      7/2005
CN     113397690 A      9/2021
(Continued)

OTHER PUBLICATIONS

International Search Report for PCT/IB2022/062316, dated Mar. 20, 2023. Searching Authority, European Patent Office, Rijswijk, Netherlands.
(Continued)

*Primary Examiner* — Khadijeh A Vahdat
(74) *Attorney, Agent, or Firm* — M&B IP Analysts, LLC

(57) ABSTRACT
A cryoprobe for cryotherapy, includes a working and a drain tube, welded together. The working tube has a first end, a distal end, an internal surface, an external surface, an inner diameter, and an outer diameter. The drain tube is placed concentrically in the working tube, and has an internal surface, an external surface, an inner diameter, an outer diameter, a first end connected to a first pressure supply, and a perforated second end which is proximate to the distal end of the working tube. The drain tube is welded to the working tube between the internal surface of the working tube and the external surface of the drain tube to manufacture a throttle perforation, in a manner which allows fluid to pass along the outer surface of the drain tube, expand at the distal end of the working tube, and drain through the drain tube.

19 Claims, 8 Drawing Sheets

(56)          References Cited

U.S. PATENT DOCUMENTS

| | | | | |
|---|---|---|---|---|
| 6,551,309 | B1 * | 4/2003 | LePivert | ................ A61B 18/02 |
| | | | | 606/23 |
| 7,519,210 | B2 | 4/2009 | Hirsch et al. | |
| 8,013,304 | B2 | 9/2011 | Haigh et al. | |
| 8,121,363 | B2 | 2/2012 | Chiakpo et al. | |
| 8,208,026 | B2 | 6/2012 | Hogasten et al. | |
| 8,450,686 | B1 | 5/2013 | Warnke et al. | |
| 8,911,147 | B2 | 12/2014 | Warnke et al. | |
| 9,198,735 | B2 | 12/2015 | Taghizadeh | |
| 2009/0171335 | A1 | 7/2009 | Cox et al. | |
| 2013/0281851 | A1 * | 10/2013 | Carr | ........................ A61B 5/01 |
| | | | | 607/96 |
| 2014/0126167 | A1 * | 5/2014 | Bozorgi | ............... B23K 26/206 |
| | | | | 219/121.64 |
| 2014/0152772 | A1 | 6/2014 | Feyh et al. | |
| 2014/0303608 | A1 | 10/2014 | Taghizadeh | |
| 2016/0153654 | A1 * | 6/2016 | Richardson, III | ...... F23C 3/004 |
| | | | | 431/160 |
| 2020/0085485 | A1 | 3/2020 | Skorich et al. | |
| 2020/0305948 | A1 | 10/2020 | Trumer et al. | |

FOREIGN PATENT DOCUMENTS

| | | | |
|---|---|---|---|
| EP | 3395275 | A1 | 10/2018 |
| WO | 2020092981 | A1 | 5/2020 |

OTHER PUBLICATIONS

Written Opinion of the Searching Authority for PCT/IB2022/062316, dated Mar. 20, 2023. Searching Authority, European Patent Office, Rijswijk, Netherlands.

* cited by examiner

200

CRYOSURGICAL PROBE AND METHOD OF MANUFACTURING THEREOF

TECHNICAL FIELD

The present disclosure relates generally to techniques in cryosurgery and specifically to techniques in use and manufacture of improved cryosurgical probes.

BACKGROUND

Cryosurgical probes operate on the principle of the Joule-Thomson effect, describing the change in temperature of real gas during the isenthalpic expansion of the gas through an orifice (a process known as throttling) from a first area to a second area, where the first area has a pressure higher than the second area.

A cryosurgical probe, also known as a cryoprobe, utilizes this dependence in pressurized cooling as gas under high pressure is expanded through a nozzle inside a cylindrical cryoprobe. Expansion of the gas cools an outer steel shell expediently, thus creating a frozen area around the tool.

An example of a tool that uses this phenomenon during medical procedures is, for example, the probe described in the patent No. EP 3 395 275 A1 or Publication No. WO 2020092981 A1.

The use of cryoprobes generating low temperature (cryogenic temperature) is widely known in medical procedures, consisting in ablation of the patient's diseased tissue by freezing it, which causes the diseased tissue's death.

Due to the size of the cryoprobe, an advantage of such solutions is the ability to focus and act directly on the diseased tissue, without damaging the healthy tissue surrounding the treatment site. Many skin treatments make use of cryo-techniques which allow avoidance of sewing and long-term healing of wounds which would otherwise result for example from the scalpel removal of lesions.

Cryosurgical probes also allow the patient to be anesthetized by freezing the axons sending the impulses responsible for pain sensation, which enables to fight pain without the side effects of taking pharmacological drugs, related to, among others, malaise or damage to the digestive system.

Known cryosurgical probes are formed using a casing covering the supply and drain ducts, and a freezing tip that is applied to the patient's tissue (the tip can be of different size and shape depending on the target).

Typical implementation of cryosurgical probes includes a single heat exchange system that provides heat exchange between an inlet tube and an outlet tube, aligned and centered inside a cylindrical housing, with the distal end (i.e., the tip) of the outlet tube acting as an expansion nozzle and being the farthest element within the probe structure.

A cryoprobe is a long, thin tool, with small elements which require a detailed manufacturing process. Due to the precision required production of such tools may be limited because of the skilled labor or specialized equipment required to produce the same.

It would therefore be advantageous to provide a solution that would overcome at least some of the manufacturing the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" or "certain embodiments" may be used herein to refer to a single embodiment or multiple embodiments of the disclosure.

Certain embodiments disclosed herein include a method for manufacturing a cryoprobe. The method comprises: inserting a drain tube into a working tube, the working tube including a first end, and a distal end, an internal surface, and external surface, an inner diameter and an outer diameter, and wherein the drain tube has a first end connected to a first pressure supply, and a perforated second end which is in proximity to the distal end; welding the drain tube to the working tube at a first anchor point and a second anchor point; and welding the drain tube to the working tube from the first anchor point to the second anchor point.

Certain embodiments disclosed herein also include a cryoprobe for cryotherapy treatments. The cryoprobe comprises: a working tube having a first end, a distal end, an internal surface, an external surface, an inner diameter, and an outer diameter; a drain tube placed concentrically in the working tube, the drain tube having an internal surface, an external surface, an inner diameter, an outer diameter, a first end connected to a first pressure supply, and a perforated second end which is proximate to the distal end of the working tube; and wherein the drain tube is welded to the working tube between the internal surface of the working tube and the external surface of the drain tube to manufacture a throttle perforation, in a manner which allows fluid to pass along the outer surface of the drain tube, expand at the distal end of the working tube, and drain through the drain tube.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1A:
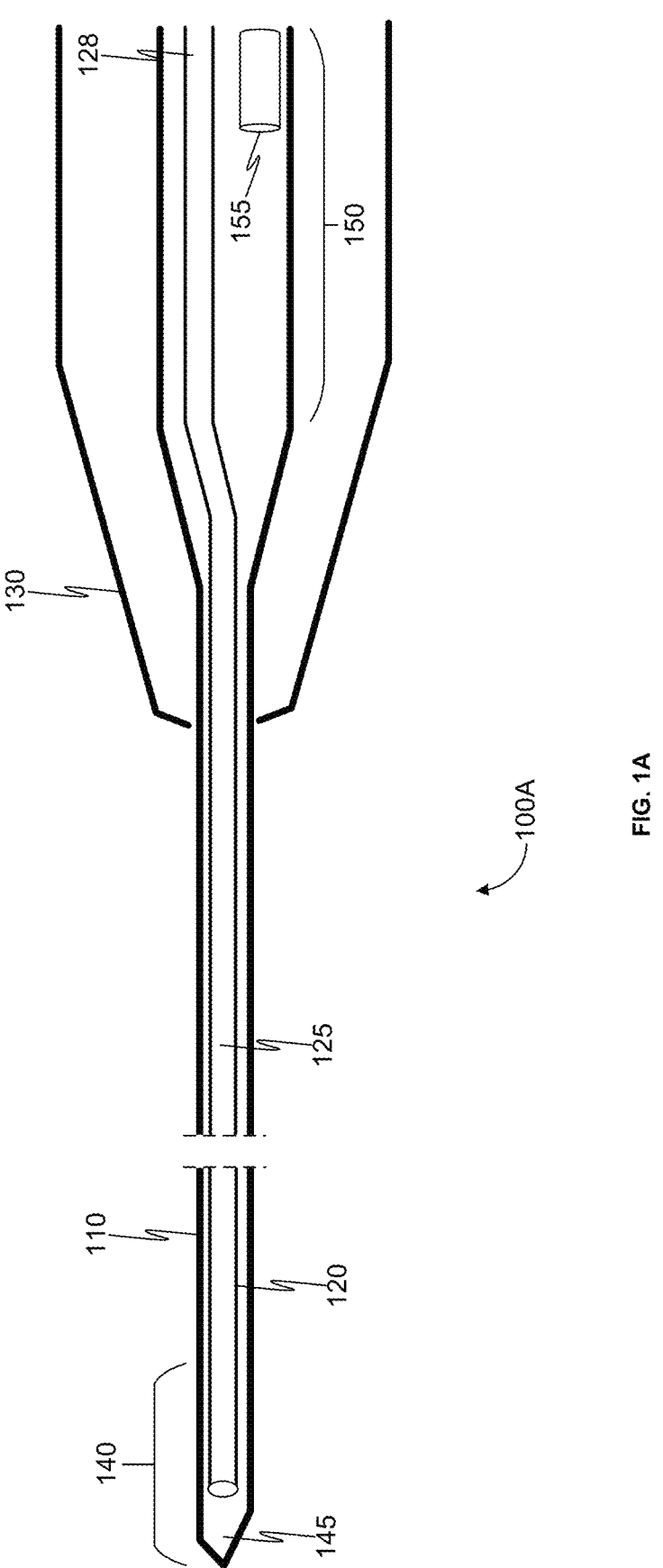
FIG. 1A is a diagram along a longitudinal section of a cryosurgical probe, implemented in accordance with an embodiment.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

A cryoprobe for cryotherapy, includes a working and a drain tube, welded together. The working tube has a first end, a distal end, an internal surface, an external surface, an inner diameter, and an outer diameter. The drain tube is placed concentrically in the working tube, and has an internal surface, an external surface, an inner diameter, an outer diameter, a first end connected to a first pressure supply, and a perforated second end which is proximate to the distal end of the working tube. The drain tube is welded to the working tube between the internal surface of the working tube and the external surface of the drain tube to manufacture a throttle perforation, in a manner which allows fluid to pass along the outer surface of the drain tube, expand at the distal end of the working tube, and drain through the drain tube.

A purpose of the disclosed embodiments is to provide a cryosurgical probe with a diameter of 0.5-0.6 mm having a tolerance of +/−10%, with a simplified structure, reduction of the number of elements and processes, while maintaining its strength and efficiency.

An embodiment according to the disclosure of a cryosurgical probe includes a thin-walled working tube casing, inside of which a discharge tube is arranged concentrically such that it is inseparably connected with an inner surface of the working tube casing along an incomplete circumference of the working tube casing surface, thus forming an opening of the expansion nozzle located between the inner surface of the working tube casing and an outer surface of the drain tube.

FIG. 1A is a diagram along a longitudinal section of a cryosurgical probe 100A, implemented in accordance with an embodiment. The cryosurgical probe 100A, also referred to herein as cryoprobe 100A, includes a working tube 110, having a first end 150 connected to a handle 130, and a distal end 140 which is used for contact with a patient.

A drain tube 120 is concentrically placed inside the working tube 110, and an inner surface of the working tube 110 is connected to an outer surface of the drain tube 120. This is explained in more detail with respect to FIG. 1B. The drain tube has a first end which is open near the distal end 145, while a second end of the drain tube is connected to a low-pressure zone, such that pressure near the distal end 140 is lower than pressure near the second end 128, resulting in suction of fluid from the distal end 140 towards the second end 128.

In an embodiment, the working tube 110 may have a first cross section at the distal end 140, and a second diameter, larger than the first diameter, at the first end 150. The working tube 110 further includes therein a refrigerant supply tube 155 which introduces at least a first type of refrigerant into the working tube 110.

The connection between the inner surface of the working tube 110 and the outer surface of the drain tube 120 is incomplete around the diameter, allowing refrigerant to flow from the supply tube 155 through the working tube, into a tip 145 of the distal end 140, and then drained through a cavity 125 of the drain tube 120. The tip 145 is also known as an expansion chamber, into which the refrigerant can expand. The expansion chamber is the coldest section of the cryoprobe 100A. Typically, ice forms around the outer surface of the cryoprobe 100A at the distal end 140. The shape of the ice formation is affected by the shape of the tip 145, meaning tips having different cross sections will result in ice formations having different forms. This may be advantageous in applications where the ice form size and shape should have certain parameters, which are beneficial to the specific treatment being applied.

Figure 1B:
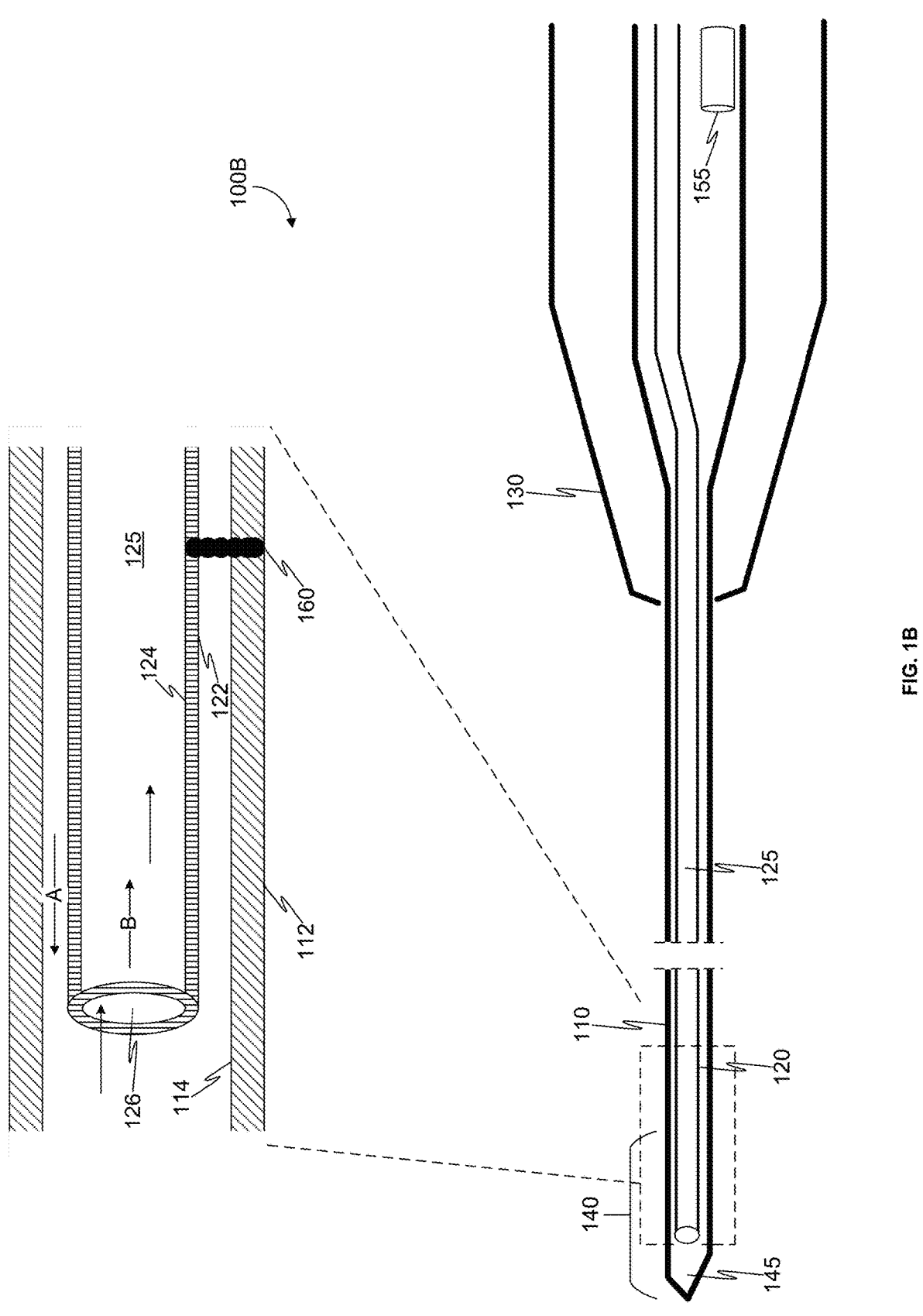
FIG. 1B is a diagram along a longitudinal section of a cryosurgical probe with an expanded view, implemented in accordance with an embodiment.

FIG. 1B is an example diagram along a longitudinal section of a cryosurgical probe 100B with an expanded view, implemented in accordance with an embodiment. The expanded view magnifies a portion of the cryoprobe in proximity to the distal end 140. In the expanded view, the drain tube 120 is shown to have an inner surface 124 which is in contact with drained refrigerant (not shown) and an outer surface 122. The outer surface 122 is welded utilizing the method described herein to the inner surface 114 of the working tube 110, where a weld point 160 extends from the outer surface 112 of the working tube 110 to at least the outer surface 122 of the drain tube 120. As the weld point 160 is not continuous across the diameter, refrigerant is able to flow, for example through at least a channel 'A'. The refrigerant is drained through opening 126 of the drain tube 120.

Figure 1C:
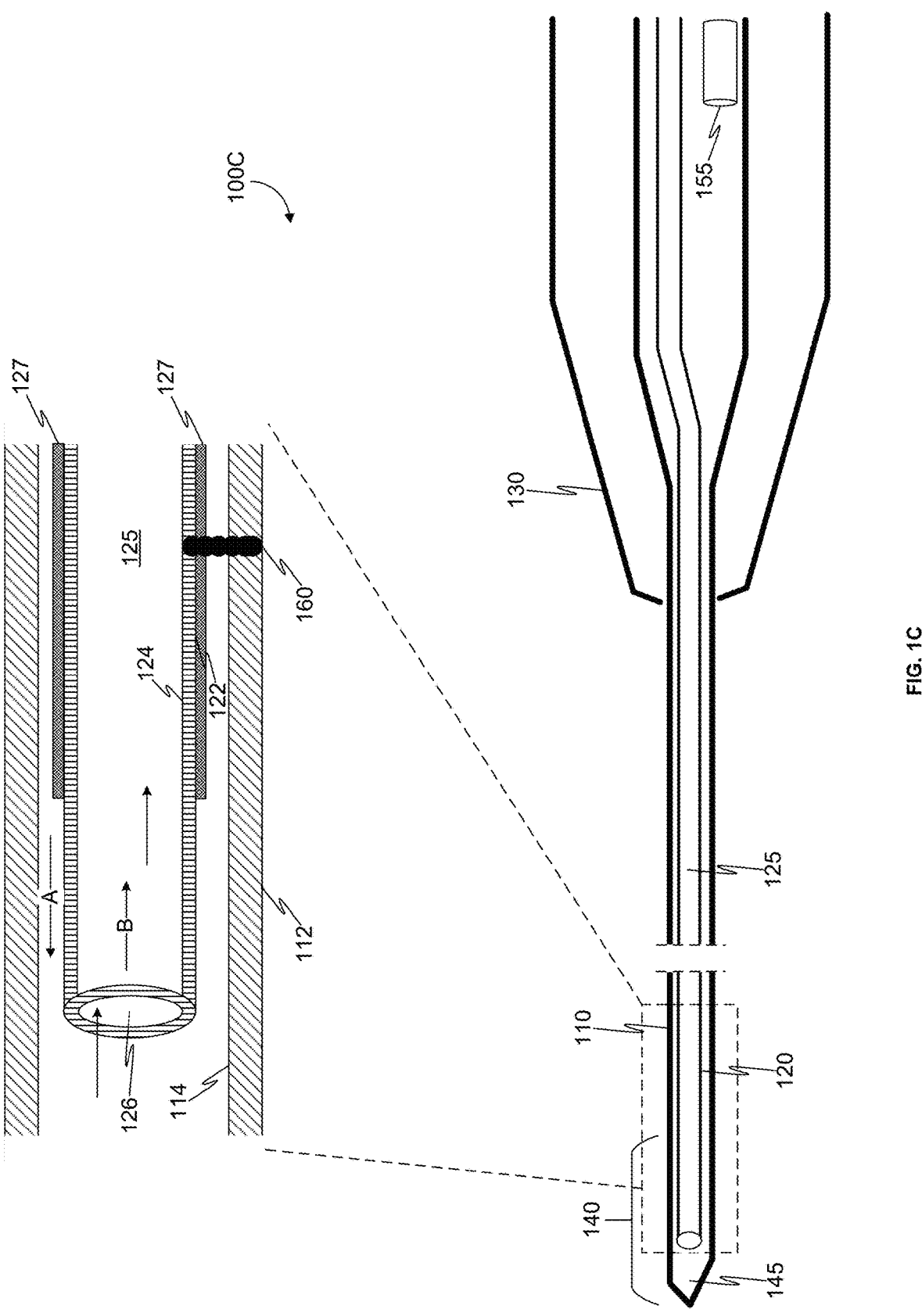
FIG. 1C is a diagram along a longitudinal section of a cryosurgical probe with an expanded view, implemented in accordance with another embodiment.

FIG. 1C is an example diagram along a longitudinal section of a cryosurgical probe with an expanded view, implemented in accordance with an embodiment. In this example, the drain tube 120 is at least partially coated with an insulating sleeve 127. The insulating sleeve 127 can be deposited on the drain tube 120, for example silicon rubber may be used to coat at least a portion of the drain tube 120 to provide for increased thermal isolation.

In an embodiment, the insulating sleeve 127 may be sleeve made of thermally insulating material which through which the drain tube 120 is placed. In an embodiment an external diameter of the insulating sleeve 127 is smaller than an internal diameter of the working tube 110. In certain embodiments, the internal diameter of the insulating sleeve 127 is equal to, or larger than, an external diameter of the drain tube 120. In some embodiments, a plurality of insulating sleeves may be utilized serially, wherein a gap is left between a first insulating sleeve and a second insulating sleeve, leaving a portion of the drain tube 120 exposed. In such embodiments, welding may be performed at the portion of the drain tube which is exposed. In certain embodiments, a stainless steel sleeve may be used to provide additional strength to the drain tube.

Figure 2:
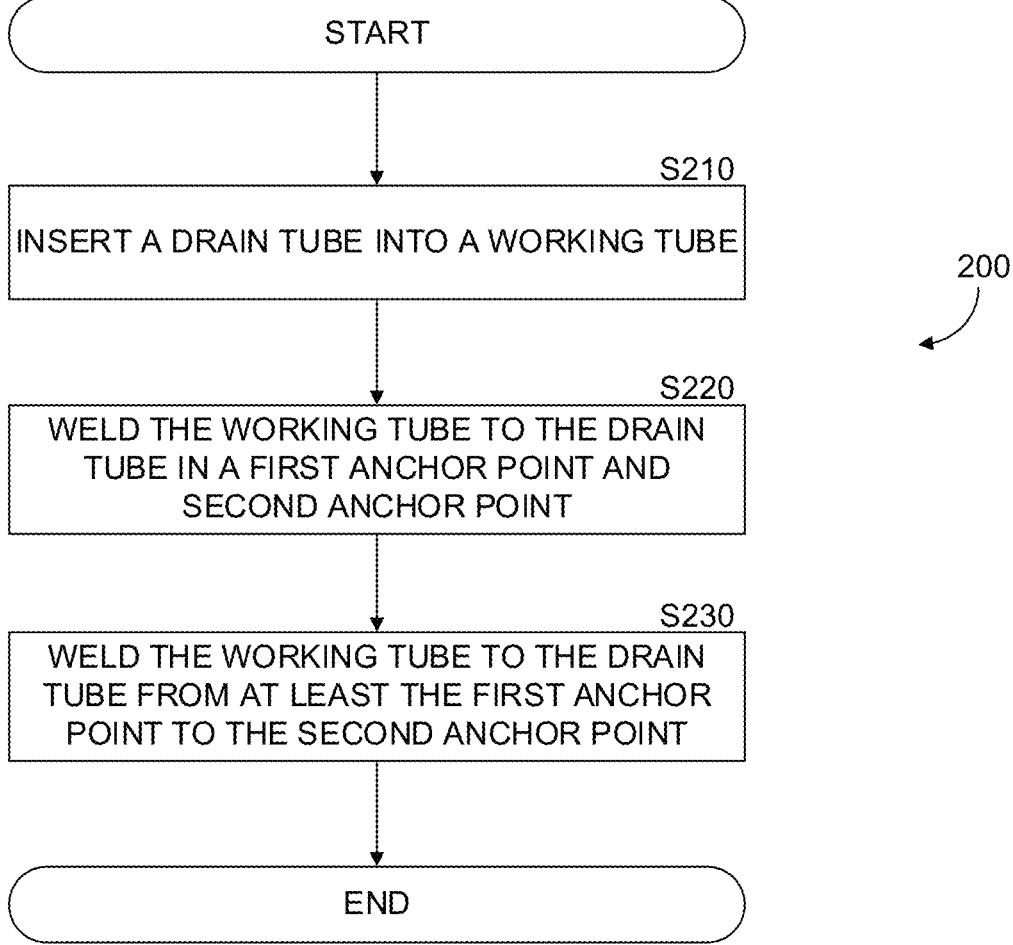
FIG. 2 is a flowchart of a method for manufacturing an improved cryosurgical probe, implemented in accordance with an embodiment.

FIG. 2 is an example flowchart 200 of a method for manufacturing an improved cryosurgical probe, implemented in accordance with an embodiment.

At S210, a drain tube is inserted into a working tube. In an embodiment, the working tube may be made of a stainless steel material. Stainless steel may be advantageous as the material is biocompatible, is a conductor of electricity, is able to withstand high pressure (around 100 bar), and has reduced heat conductivity. Conducting electric current allows the cryoprobe to deliver neurostimulation pulses, which is beneficial in some applications.

The working tube has a diameter which is larger than the diameter of the drain tube. In an embodiment, the working tube inner diameter is larger by 1 mm (with a tolerance of 10%) than the drain tube outer diameter. Thus, the distance between the out surface of the drain tube and the inner surface of the working tube is approximately 0.05 mm (with a tolerance of 10%) in such embodiments.

At S220, the working tube is welded to the drain tube in at least a first anchor point and a second anchor point. In an embodiment, explored in more detail in FIG. 3 below, the working tube is welded to the drain tube at 4 anchor points, which allows for additional stability. Welding the working tube to the drain tube may be performed, for example, by a laser (laser welding, micro welding, or laser sealing), such as a flash lamp pumped solid state laser, diode pumped solid state laser, fiber laser, CO based laser, $CO_2$ based laser, and the like. In an embodiment, emission wavelength of the laser may be between 1030 nm and 1080 nm, to ensure high absorption rate in stainless steel. As another example, a wavelength of 532 nm may be used to ensure high absorption rate in copper based tubes, for example using a neodymium-doped yttrium aluminum garnet (Nd:YAG) laser.

In an embodiment, a flash lamp pumped Nd:YAG laser having a maximum power peak of 7.5 kW, maximum average power of 60 W may be used with a pulse duration between 0.3 and 25 ms, with a repetition rate up to 20 Hz, to generate anchor points which are between 0.2 to 2 mm in size. In another embodiment, an anchor point of 0.2 mm to 0.5 mm may be generated using between 5% to 10% of the previously mentioned Nd:YAG laser, with a pulse duration of 8.6 ms, and a repetition rate of 2 Hz.

It should be readily apparent that beam size is a tradeoff between precision of the welding process (i.e., achievable minimal diameter of a throttle, which is the area through which fluid can flow between the working tube and drain tube) and productivity. Productivity is measured in a lower number of laser spots needed to cover the desired interaction path (the area which is constricted by the weld). The smaller the beam diameter, the higher precision; the larger the diameter, the higher productivity. Thus, other configurations are possible. and the disclosed embodiments are present here as non-limiting examples.

At S230, the working tube is welded to the drain tube between at least the first anchor point and the second anchor point. Thus, a portion of the area defined between the outer surface of the drain tube and the inner surface of the working tube is restricted, thus constricting the ability of fluids to flow therein between. The area where the flow may continue is known as the throttle, and shown in greater detail with respect to FIG. 3D below.

In an embodiment, an inert shielding gas, such as Argon (Ar) is used during the welding process to mitigate the risk of welding point corrosion. In certain embodiments, a flow of a gas, such as Nitrogen (N), is provided to the working tube and drained through the drain tube. The flow of gas is monitored, (for example using a flow meter attached to the drain tube) and the welding process is stopped when the flow is at a predetermined rate. In an embodiment, a number of pulses and their spatial separation define the flow-rate of a gas through the throttle.

Figure 3A:
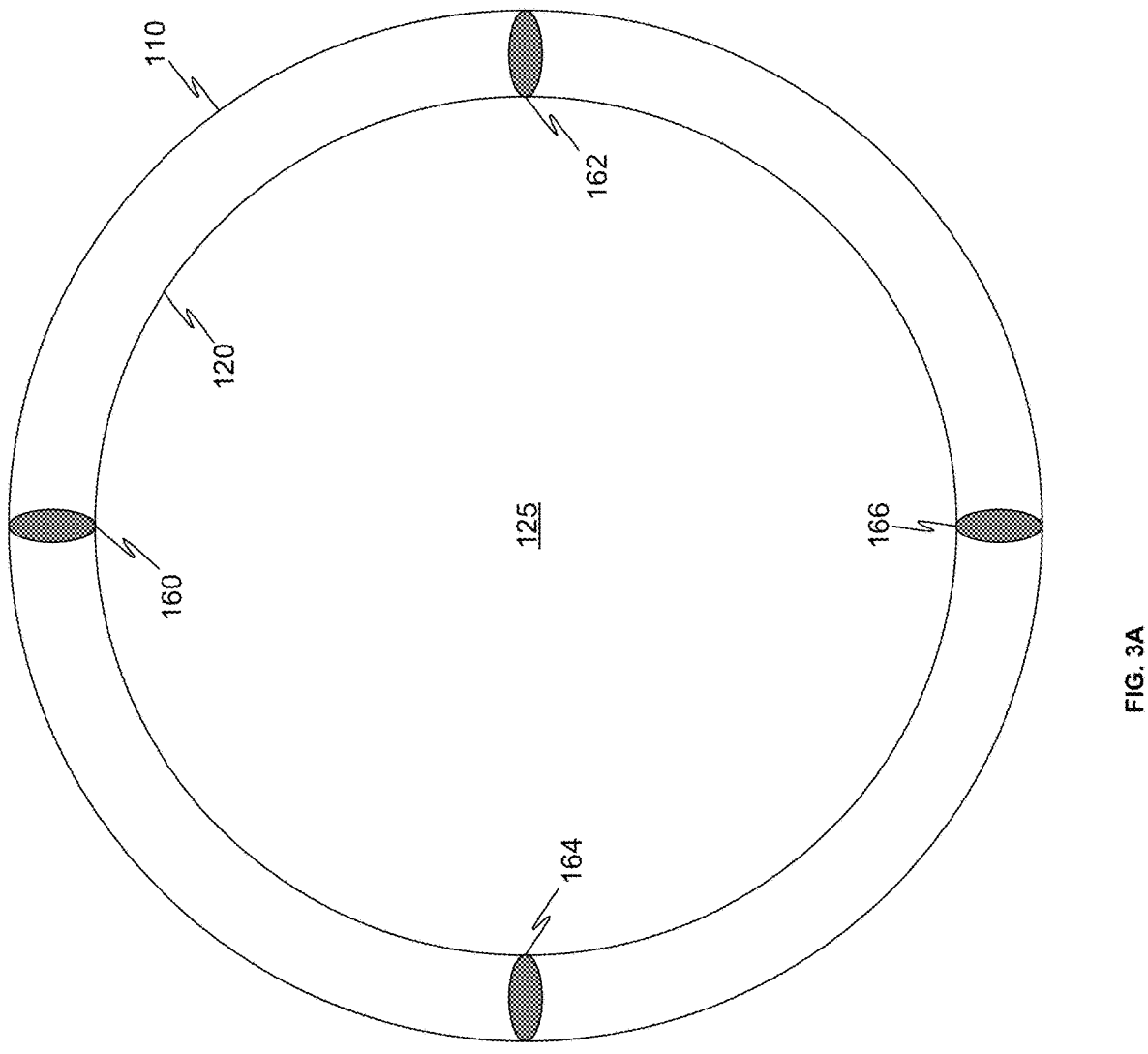
FIG. 3A is a schematic illustration of a cross section view of a first phase in manufacturing a cryosurgical probe, implemented in accordance with an embodiment.

Reference is now made to FIGS. 3A through 3D, which illustrate the steps of a method for manufacturing a cryosurgical probe, in accordance with an embodiment. FIG. 3A is a schematic illustration of a cross section view of a first phase 300A in manufacturing a cryosurgical probe, implemented in accordance with an embodiment. In the first phase of manufacturing anchor points are created to weld together the working tube 110 and the drain tube 120. Welding occurs from the outside, for example, by focusing a laser beam at the working tube 110. A first anchor point 160 is created across from a fourth anchor point 166, and a second anchor point 162 is created across from a third anchor point 164. While this example has the anchor points across from each other and equidistant on the working tube 110 perimeter, it is understood that other placements of anchor points may be utilized without departing from the scope of this disclosure.

Figure 3B:
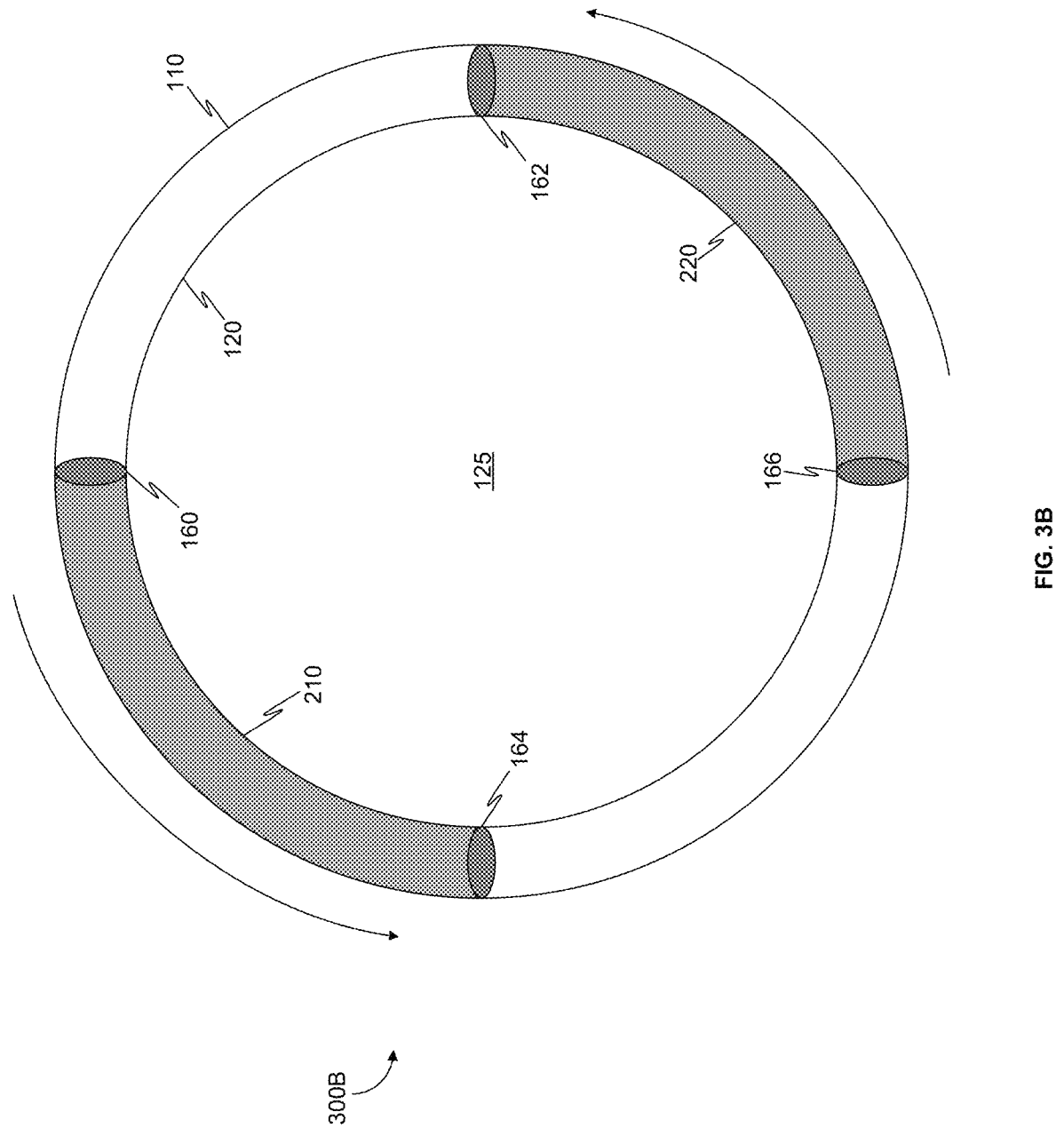
FIG. 3B is a schematic illustration of a cross section view of a second phase in manufacturing a cryosurgical probe, implemented in accordance with an embodiment.

FIG. 3B is a schematic illustration of a cross section view of a second phase 300B in manufacturing a cryosurgical probe, implemented in accordance with an embodiment. In the second phase, multiple point welds are created, for example, by forming the laser beam in a counter-clockwise pattern, from the first anchor point 160 to the third anchor point 164, and from the fourth anchor point 166 to the second anchor point 162. In an embodiment, both sections may be done at the same time, using one or more laser welding systems. This results in a first welded area 210 and a second welded area 220, which result in a strong bond between the working tube and drain tube. While the area is shown as contiguous in the illustration, it is understood that this area is in fact made up of multiple spot welds, which have a certain degree of overlap between them.

Figure 3C:
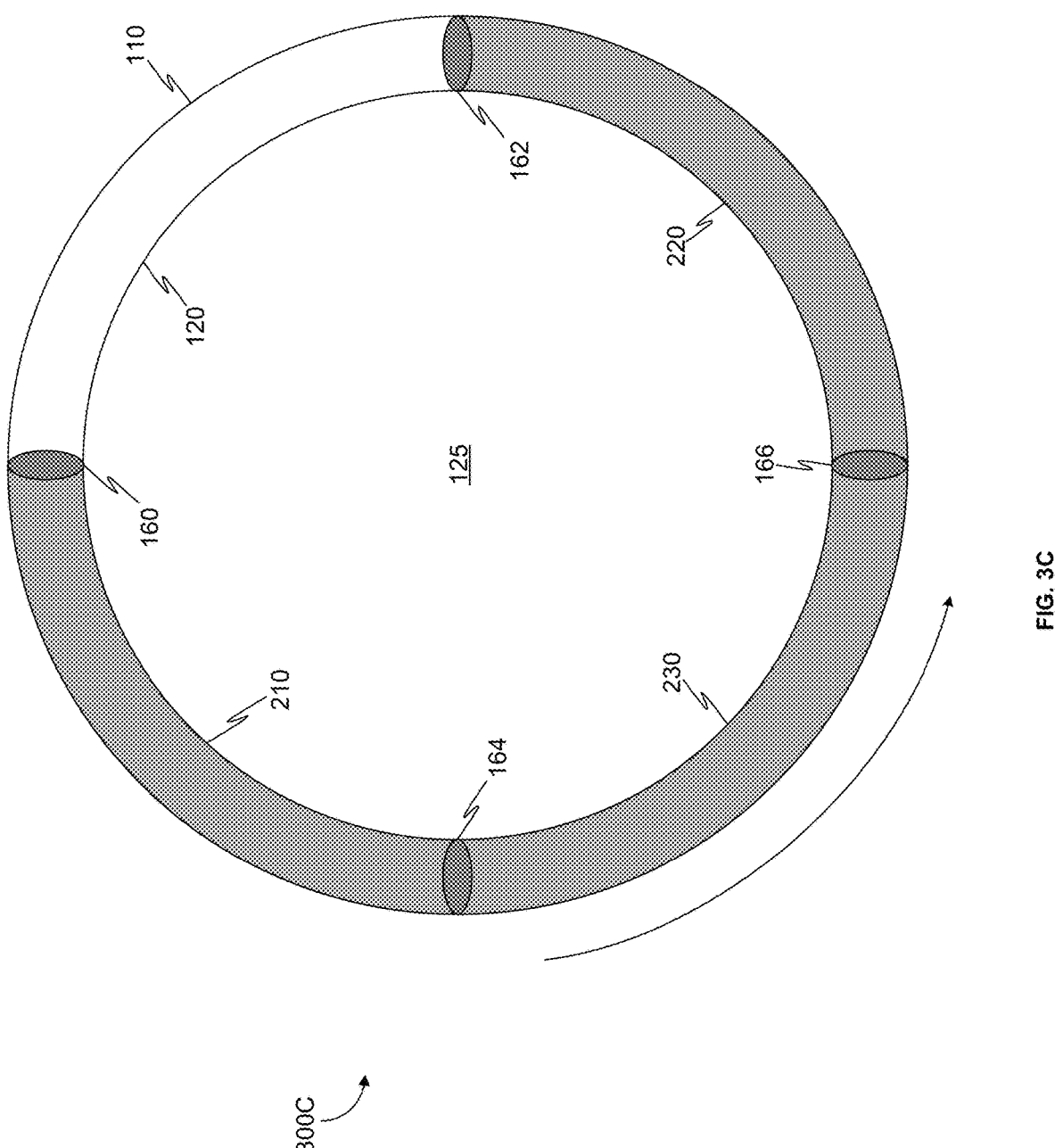
FIG. 3C is a schematic illustration of a cross section view of a third phase in manufacturing a cryosurgical probe, implemented in accordance with an embodiment.

FIG. 3C is a schematic illustration of a cross section view of a third phase 300C in manufacturing a cryosurgical probe, implemented in accordance with an embodiment. In the third phase additional weld points are created, between the third anchor point 164 and the fourth anchor point 166. This may likewise be performed counter-clockwise, resulting in a third welded area 230. As before the area is shown as contiguous in the illustration, however it is understood that this area is in fact made up of multiple spot welds, which have a certain degree of overlap between them.

Figure 3D:
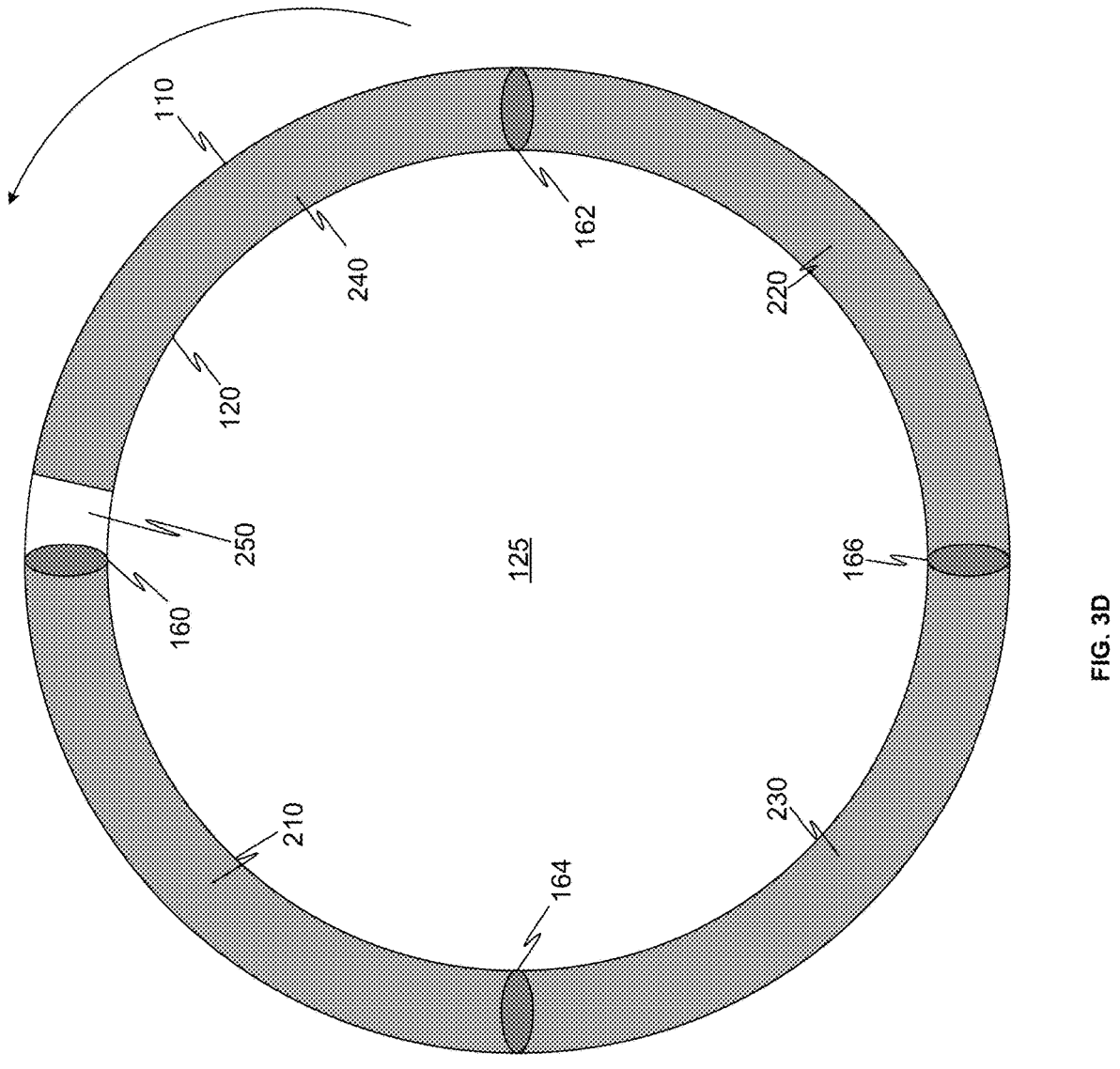
FIG. 3D is a schematic illustration of a cross section view of a fourth phase in manufacturing a cryosurgical probe, implemented in accordance with an embodiment.

FIG. 3D is a schematic illustration of a cross section view of a fourth phase 300D in manufacturing a cryosurgical probe, implemented in accordance with an embodiment. In the fourth phase yet additional weld points are created, beginning at the second anchor point 162, and stopping shy of the first anchor point 160, resulting in a fourth welded area 240, and a throttle 250. Throttle 250 constricts the flow of fluid between the first end of the working tube, and the distal end, resulting in the Joule-Thomson effect of cooled expanded fluid. In an embodiment, a plurality of throttles, may be created. In certain embodiments, a first group of throttles may have a first size, and a second group of throttles may have a second size, which is different than the first size.

According to an embodiment, one advantage of the disclosure is a cryosurgical probe with an external diameter of 1 mm. Due to the passage of the refrigerant from the supply tube into the space defined between the casing and the drain tube, the thicknesses of the supply tube and the nozzle can be omitted and thus the diameter of the cryosurgical probe tip can be significantly reduced compared to prior art solutions.

According to another embodiment, a gas, after decompression, drained through the drain tube, is in contact with the supply duct, which results in a transition of the refrigerant from a gaseous state to a liquid-gas mixture and maintains am ambient temperature in this area of the probe. This ensures that the treatment will not injure or damage tissues in undesirable places. Additionally, such configuration prevents the spread of low temperature to the probe handle, which is safer for the operator of the device and reduces harm through injury.

Another advantage in utilizing the teachings herein is the ability to dispense with the use of vacuum insulation, which is a frequent element of other known solutions in the construction of cryosurgical probes.

Yet another advantage is the ability to reduce the gap (i.e., increasing the length of the circumferential weld) after manufacturing and product inspection, which is impossible with the use of nozzles having a constant diameter in the prior art.

Furthermore, by connecting the internal elements (i.e., drain tube) of the cryoprobe from the outside, no additional closing or sealing elements are required, thus resulting in a more robust solution.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; 2A; 2B; 2C; 3A; A and B in combination; B and C in combination; A and C in combination; A, B, and C in combination; 2A and C in combination; A, 3B, and 2C in combination; and the like.

What is claimed is:

1. A method for manufacturing a cryoprobe, comprising:
inserting a drain tube into a working tube, wherein the working tube includes a first end, and a distal end, an internal surface, and external surface, an inner diameter and an outer diameter, and wherein the drain tube has a first end connected to a first pressure supply, and a perforated second end which is in proximity to the distal end;
welding the drain tube to the working tube at a first anchor point and a second anchor point; and
welding the drain tube to the working tube from the first anchor point to the second anchor point such that there is at least a non-welded gap between the first anchor point and the second anchor point;
wherein the working tube and the drain tube are adapted to enable a refrigerant to flow from a refrigerant supply tube through the working tube but exterior to the drain tube past the gap and into a tip at a distal end of the working tube from which the refrigerant then passes from the tip the drain tube.

2. The method of claim 1, wherein welding is performed using at least one of: a flash lamp pumped solid state laser, a diode pumped solid state laser, a fiber laser, a Carbon monoxide (CO) based laser, and a $CO_2$ based laser.

3. The method of claim 1, wherein welding is performed by a neodymium-doped yttrium aluminum garnet (Nd: YAG) laser.

4. The method of claim 3, wherein the Nd: YAG laser has a maximum power peak of 7.5 kW, maximum average power of 60 W, and a pulse duration between 0.3 and 25 ms with a repetition rate up to 20 Hz.

5. The method of claim 3, wherein the Nd: YAG laser has a pulse duration of 8.6 ms, and a repetition rate of 2 Hz.

6. The method of claim 1, further comprising:
inserting an inert shielding gas between the working tube and the drain tube.

7. The method of claim 1, wherein the drain tube is at least partially covered by a thermally insulating sleeve.

8. The method of claim 1, wherein inner diameter of the working tube is 1 mm, with a tolerance of 10%, larger than an outer diameter of the drain tube.

9. The method of claim 1, wherein the working tube, the drain tube, or both include stainless steel.

10. The method of claim 1, wherein the working tube, the drain tube, or both, include copper.

11. A cryoprobe for cryotherapy, comprising:
a working tube having a first end, a distal end, an internal surface, an external surface, an inner diameter, and an outer diameter;
a drain tube placed concentrically in the working tube, the drain tube having an internal surface, an external surface, an inner diameter, an outer diameter, a first end connected to a first pressure supply, and a perforated second end which is proximate to the distal end of the working tube; and
wherein the drain tube is welded to the working tube between the internal surface of the working tube and the external surface of the drain tube to manufacture a throttle perforation, in a manner which allows fluid to pass through the working tube along the external surface of the drain tube, expand at the distal end of the working tube, and drain through the drain tube.

12. The cryoprobe of claim 11, wherein welding the drain tube to the working tube is performed using at least one of: a flash lamp pumped solid state laser, a diode pumped solid state laser, a fiber laser, a CO based laser, a $CO_2$ based laser.

13. The cryoprobe of claim 11, wherein welding the drain tube to the working tube is performed by a neodymium-doped yttrium aluminum garnet (Nd: YAG) laser.

14. The cryoprobe of claim 13, wherein the Nd: YAG laser has a maximum power peak of 7.5 kW, maximum average power of 60 W, and a pulse duration between 0.3 and 25 ms with a repetition rate up to 20 Hz.

15. The cryoprobe of claim 13, wherein the Nd: YAG laser has a pulse duration of 8.6 ms, and a repetition rate of 2 Hz.

16. The cryoprobe of claim 11, wherein the drain tube is at least partially covered by a sleeve.

17. The cryoprobe of claim 11, wherein inner diameter of the working tube is 1 mm, with a tolerance of 10%, larger than an outer diameter of the drain tube.

18. The cryoprobe of claim 11, wherein the working tube, the drain tube, or both include stainless steel.

19. The cryoprobe of claim 11, wherein the working tube, the drain tube, or both, include copper.

* * * * *